(12) United States Patent
Blackaby et al.

(10) Patent No.: US 6,730,676 B2
(45) Date of Patent: May 4, 2004

(54) PYRAZINO-PYRIDAZINE DERIVATIVES AS LIGANDS FOR GABA RECEPTORS

(75) Inventors: Wesley Peter Blackaby, Buckhurst Hill (GB); Richard Thomas Lewis, Bishops Stortford (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 11 days.

(21) Appl. No.: 10/168,234

(22) PCT Filed: Jan. 8, 2001

(86) PCT No.: PCT/GB01/00058
§ 371 (c)(1),
(2), (4) Date: Jun. 18, 2002

(87) PCT Pub. No.: WO01/51492
PCT Pub. Date: Jul. 19, 2001

(65) Prior Publication Data
US 2003/0013716 A1 Jan. 16, 2003

(30) Foreign Application Priority Data
Jan. 11, 2000 (GB) .............................. 0000564

(51) Int. Cl.$^7$ ................ C07D 487/04; A61K 31/4985; A61K 31/5025
(52) U.S. Cl. ................ 514/249; 514/228.5; 514/232.5; 514/234.2; 514/211.08; 544/118; 544/236; 544/61; 544/81; 540/553; 540/575
(58) Field of Search ............................. 514/249, 228.5, 514/232.5, 234.2, 211.08; 544/118, 81, 236, 61; 540/553, 575

(56) References Cited

U.S. PATENT DOCUMENTS

| | | | |
|---|---|---|---|
| 5,182,386 A | 1/1993 | Albaugh et al. | 540/350 |
| 5,380,719 A | 1/1995 | Kim | 514/85 |

FOREIGN PATENT DOCUMENTS

| | | |
|---|---|---|
| WO | WO 92/07853 | 5/1992 |
| WO | WO 98/04559 | 2/1998 |
| WO | WO 98/22466 | 5/1998 |
| WO | WO 98/50385 | 11/1998 |
| WO | WO 99/00391 | 1/1999 |
| WO | WO 99/06406 | 2/1999 |
| WO | WO 99/25353 | 5/1999 |
| WO | WO 00/44752 | 8/2000 |

OTHER PUBLICATIONS

Chemical Abstracts, vol. 66, No. 9, Feb. 27, 1967 abstract No. 37890d, p. 3615; N.R. Patel et al.: J. Heterocycl. Chem., vol. 3, No. 4, 1966, paged 512–7.
Chemical Abstracts, vol. 66, No. 3, Jan. 16, 1967 abstract No. 10902v. p. 1058; V. Sprio et al.: Ann. Chim., vol. 56, No. 8–9, 1966, pp. 866–873.

*Primary Examiner*—John M Ford
(74) *Attorney, Agent, or Firm*—J. Eric Thies; Melvin Winokur

(57) ABSTRACT

A class of pyrazino[2,3-d]pyridazine derivatives, possessing an optionally substituted cycloalkyl, phenyl or heteroaryl substituent at the 5-position, a substituted alkoxy moiety at the 3-position, and a range of substituents at the 2-position, are selective ligands for $GABA_A$ receptors, in particular having high affinity for the α2 and/or α3 and/or α5 subunit thereof, and are accordingly of benefit in the treatment and/or prevention of adverse conditions of the central nervous system, including anxiety, convulsions and cognitive disorders.

9 Claims, No Drawings

PYRAZINO-PYRIDAZINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB01/00058, filed Jan. 8, 2001, which claims priority under 35 U.S.C. §119 form GB Application No. 0000564.5, Jan. 11, 2000.

The present invention relates to a class of substituted pyrazino-pyridazine derivatives and to their use in therapy. More particularly, this invention is concerned with substituted pyrazino[2,3-d]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 5\beta 3\gamma 2/3$, $\alpha 6\beta \gamma 2$, $\alpha 6\beta \delta$ and $\alpha 4\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta \gamma 2$ and $\alpha 3\beta \gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta \gamma 2$, $\alpha 2\beta \gamma 2$ or $\alpha 3\beta \gamma 2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation Moreover, agents which are inverse agonists of the $\alpha 5$ subunit are likely to be beneficial in enhancing cognition, for example in subjects suffering from dementing conditions such as Alzheimer's disease. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

The present invention provides a class of pyrazino-pyridazine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

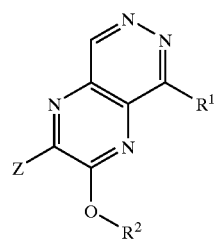

(I)

wherein

Z represents $C_{1-6}$ alkyl, $C_{3-7}$ cycloalkyl, $C_{4-7}$ cycloalkenyl, $C_{6-8}$ bicycloalkyl, aryl, $C_{3-4}$ heterocycloalkyl, heteroaryl or di($C_{1-6}$)alkylamino, any of which groups may be optionally substituted;

$R^1$ represents $C_{3-7}$ cycloalkyl, phenyl, furyl, thienyl or pyridinyl, any of which groups may be optionally substituted; and $R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

The groups Z, $R^1$ and $R^2$ may be unsubstituted, or substituted by one or more, suitably by one or two, substituents. In general, the groups Z, $R^1$ and $R^2$ will be unsubstituted or monosubstituted. Examples of optional substituents on the groups Z, $R^1$ and $R^2$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$) alkoxy. Particular substituents include methyl, ethyl and fluoro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, sec-butyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical $C_{6-8}$ bicycloalkyl groups include bicyclo[2.1.1] hexyl and bicyclo [2.2.1]heptyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Examples of suitable values for the substituent Z include methyl, ethyl, isopropyl, sec-butyl, tert-butyl, 1,1-dimethylpropyl, cyclopropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, phenyl, pyrrolidinyl, methyl-pyrrolidinyl, piperidinyl, morpholinyl, thiomorpholinyl, pyridinyl, furyl, thienyl, chloro-thienyl and diethylamino.

Specific values of Z include sec-butyl, tert-butyl, cyclopropyl, cyclohexyl, phenyl, furyl and thienyl.

Examples of typical optional substituents on the group $R^1$ include methyl, fluoro and methoxy, especially fluoro.

Representative values of $R^1$ include cyclopropyl, phenyl, methylphenyl, fluorophenyl, difluorophenyl, methoxyphenyl, furyl, thienyl, methyl-thienyl and pyridinyl. More particularly, $R^1$ may represent unsubstituted, mono-substituted or disubstituted phenyl. Most particularly, $R^1$ represents phenyl, fluorophenyl or difluorophenyl, especially phenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^2$ represents an optionally substituted triazolyl-methyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl, especially $C_{1-6}$ alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl or ethyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylamino-carbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, iso-quinolinylnethyl and quinoxalinylmethyl.

Favoured values of $R^2$ include methyl-triazolylmethyl an ethyl-triazolylmethyl.

A particular sub-class of compounds according to the invention is represented by the compounds of formula IIA, and salts and prodrugs thereof:

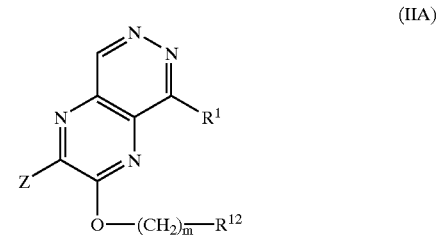

(IIA)

wherein

Z and $R^1$ are as defined with reference to formula I above;

m is 1 or 2, preferably 1; and $R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted by one or more substituents.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl, especially $C_{1-6}$ alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl or ethyl.

Particular values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, ethyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methyl-piperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Favoured values of $R^{12}$ include methyl-triazolyl and ethyl-triazolyl.

A particular subset of the compounds of formula IIA above is represented by the compounds of formula IIB, and pharmaceutically acceptable salts thereof:

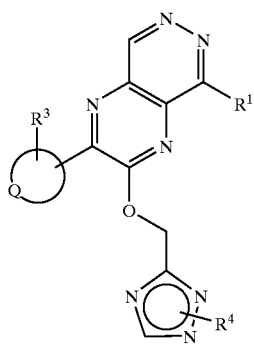

(IIB)

wherein $R^1$ is as defined with reference to formula I above;

Q represents the residue of a cyclopropyl, cyclobutyl, cyclopentyl, cyclohexyl, phenyl, furyl or thienyl ring;

$R^3$ represents hydrogen, methyl or fluoro; and $R^4$ represents methyl or ethyl.

In relation to formula IIB above, $R^1$ suitably represents phenyl, fluorophenyl or difluorophenyl, especially phenyl.

In a particular embodiment, Q suitably represents the residue of a cyclobutyl ring. In another embodiment, Q represents the residue of a cyclopropyl or cyclohexyl ring. In a further embodiment, Q represents the residue of a phenyl, furyl or thienyl ring.

Suitably, $R^3$ represents hydrogen.

In a particular embodiment $R^4$ suitably represents methyl. In another embodiment, $R^4$ represents ethyl.

Specific compounds within the scope of the present invention include:

2-cyclohexyl-3-(2-ethyl-2H-[1,2,4]triazol-3-ylmethoxy)-5-phenylpyrazino[2,3-d]pyridazine;
2-sec-butyl-3-(2-ethyl-2H-[1,2,4]triazol-3-ylmethoxy)-5-phenylpyrazino[2,3-d]pyridazine;
2-cyclopropyl-3-(2-ethyl-2H-[1,2,4]triazol-3-ylmethoxy)-5-phenylpyrazino[2,3-d]pyridazine;
3-(2-ethyl-2H-[1,2,4]triazol-3-ylmethoxy)-2-(furan-2-yl)-5-phenylpyrazino[2,3-d]pyridazine;
2-tert-butyl-3-(2-ethyl-2H-[1,2,4]triazol-3-ylmethoxy)-5-phenylpyrazino[2,3-d]pyridazine;
2-tert-butyl-3-(1-methyl-1H-[1,2,4]triazol-3-ylmethoxy)-5-phenylpyrazino[2,3-d]pyridazine;
2,5-diphenyl-3-(2-ethyl-2H-[1,2,4]triazol-3-ylmethoxy) pyrazino[2,3-d]pyridazine;
2,5-diphenyl-3-(1-methyl-1H-[1,2,4]triazol-3-ylmethoxy) pyrazino[2,3-d]pyridazine;
3-(2-methyl-2H-[1,2,4]triazol-3-ylmethoxy)-5-phenyl-2-(2-thienyl)-pyrazino[2,3-d]pyridazine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 21, 101–108.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III (or its 2-hydroxypyrazino[2,3-d]pyridazine tautomer) with a compound of formula IV:

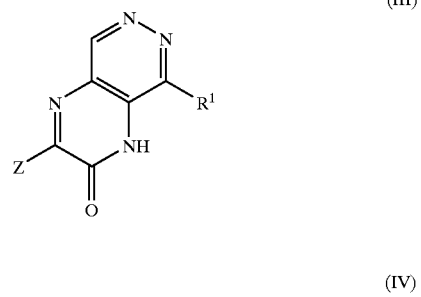

wherein Z, $R^1$ and $R^2$ are as defined above, and $L^1$ represents a suitable leaving group.

The leaving group $L^1$ is suitably the moiety formed when a hydroxy group reacts with triphenylphosphine in the presence of diethylazodicarboxylate.

The reaction between compounds III and IV is conveniently effected by stirring the reactants in a suitable solvent, typically dichloromethane.

The precursors to the intermeidates of formula IV above, where $L^1$ is hydroxy, may be prepared by the procedures described in WO 98/04559, or by methods analogous thereto.

Where they are not commercially available, the starting materials of formula III may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (–)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 or α5 subunit stably expressed in Ltk$^-$ cells.

The compounds of the accompanying Examples have all been found to possess a $K_i$ value for displacement of [$^3$H]-flumazenil from the α2 and/or α3 and/or α5 subunit of the human $GABA_A$ receptor of 100 nM or less.

EXAMPLE 1

2-Cyclohexyl-3-(2-ethyl-2H-[1,2,4]triazol-3-ylmethoxy)-5-phenylpyrazino[2,3-d]pridazine a) 4-Amino-6-phenyl-3(2H)-pyridazinone

To acetophenone (250 g, 2 mol) was added glyoxylic acid (61.37 g, 0.66 mol) and the mixture heated at 105° C. for 3 hours. After cooling to room temperature the reaction was diluted with water followed by concentrated (0.880) aqueous ammonia (53 ml). The unreacted acetophenone was extracted into dichloromethane and recovered. The ammoniacal solution was stirred with hydrazine hydrate (33 ml) and heated at reflux for two hours. The solid which precipitated on cooling was collected by filtration then added to hydrazine hydrate (550 ml) and the mixture heated at reflux for 12 hours. The solid was collected by filtration, washed with water followed by cold acetonitrile and dried under vacuum to give a white solid (73.9 g; 59.3%). $^1$H NMR (400 MHz, DMSO-$d_6$) δ12.66 (1H, bs), 8.91 (1H, s), 7.72 (2H, m), 7.41 (1H, m), 6.73 (1H, s) 6.43 (2H, bs); m/e (ES$^+$) 188 [MH]$^+$.

b) 4-Amino-5-bromo-6-phenyl-3(2H)-pyridazinone

4-Amino-6-phenyl-3(2H)-pyridazinone (prepared by the method of Example 1a), or according to McKillop et al., *Heterocycles*, 1989, 29(6), 1077) (4.69 g, 25 mmol) and N-bromosuccinimide (4.50 g, 25.3 mmol), suspended in dry acetonitrile (135 ml), was heated at reflux under a nitrogen atmosphere for 6 hours, then allowed to stand at room temperature for 18 hours. The solid was collected by filtration, washed with ethyl acetate (40 ml) and diethyl ether (40 ml), and dried in vacuo at 60° C., to afford the title compound, 6.25 g (94%), as a colourless solid. $^1$H NMR (400 MHz, DMSO-$d_6$) δ12.93 (1H, s), 7.43 (5H, m), 6.69 (2H, br s); m/e (ES$^+$) 266/268 [MH]$^+$.

c) 4-[Bis(tert-butoxycarbonyl)amido]-5-bromo-6-phenyl-3(2H)-pyridazinone

To the product of Example 1b) (25 g, 94 mmol), and 4-dimethylaminopyridine (0.44 g), suspended in dry N,N-dimethylformamide (250 ml), was added, with stirring, di-tert-butyl dicarbonate (62 g) portionwise. On completion of addition, the mixture was stirred an additional 2 hours at room temperature, then most of the solvent was stripped at reduced pressure. The residue was partitioned between ethyl acetate and water, and the organic phase separated and washed with water, evaporated, and the residue azeotroped with toluene at reduced pressure to afford a yellow foam. This was dissolved in warm methanol (500 ml), silica gel (flash chromatography grade, 80 g) added, and the mixture was stirred at room temperature for 36 hours. The reaction was then diluted with dichloromethane (1.5 l) and the silica removed by filtration. The filtrate was evaporated at reduced pressure, and the residue crystallised from diethyl ether and isohexane and dried in vacuo at 40° C., to afford the title compound, 31.28 g (71%), as a colourless solid. $^1$H NMR (400 MHz, DMSO-$d_6$) δ13.79 (1H, s), 7.49 (5H, m), 1.40 (18H, s); m/e (ES$^+$) 310/312 [MH-Boc-(CH$_3$)$_2$CCH$_2$)]$^+$, 266/268 [MH-2Boc]$^+$.

d) 5-Azido-4-[bis(tert-butoxcyarbonyl)amidol-6-phenyl-3(2H)-pyridazinone

To the product of Example 1c) (31 g, 67 mmol) in dry N,N-dimethylformamide (100 ml) was added, with stirring, tetramethylguanidinium azide (12 g, 1.1 equivalents), and the solution was then heated at 70° C. for 20 hours (behind a perspex blast screen). The reaction mixture was cooled to room temperature then most of the solvent was stripped at reduced pressure. The residue was diluted with ethyl acetate (150 ml) and washed with water (2×100 ml), then brine (50 ml). The organic phase was evaporated, and the residue was crystallised from diethyl ether/isohexane and dried in vacuo at 30° C., to afford the title compound, 24.7 g (86%), as a pale yellow solid, m.p. 149–150° C. dec. $^1$H NMR (400 MHz, DMSO-$d_6$) δ13.57 (1H, s), 7.58 (2H, m), 7.49 (3H, m), 1.43 (18H, s).

e) 5-Amino-4-[bis(tert-butoxycarbonyl)amido]-6-phenyl-3(2H)-pyridazinone

To the product of Example 1d) (24.7 g, 57.6 mmol), in dichloromethane (100 ml) and ethanol (400 ml), was added under nitrogen 10% palladium on carbon (2.5 g). The mixture was then hydrogenated under an atmosphere of hydrogen gas, with stirring, for 18 hours. The catalyst was removed by filtration, and the filter cake washed well with 10% ethanol in dichloromethane. Most of the solvent was stripped from the combined filtrates at reduced pressure. The residue was crystallised from ethanol and dried in vacuo at 40° C., to afford the title compound, 23 g (99%). $^1$H NMR (400 MHz, DMSO-$d_6$) δ12.40 (1H, s), 7.48 (3H, m), 7.43 (2H, m), 5.95 (2H, br s), 1.38 (18H, s); m/e (ES$^+$) 403 MH]$^+$, 247 [MH-Boc-(CH$_3$)$_2$CCH$_2$)]$^+$.

f) 4,5-Diamino-6-phenyl-3(2H)-pyridazinone Hydrochloride

To the product of Example 1e) (23 g, 57 mmol) was added a saturated solution of hydrogen chloride in methanol (500 ml), and the resulting solution allowed to stand for 18 hours under a nitrogen atmosphere. The solvent was stripped at reduced pressure, and the residue azeotroped with toluene to afford a hydrochloride salt of unknown stoichiometry as a yellow foam, which was dried in vacuo at 40° C., and used without further purification. m/e (ES$^+$) 203 [MH]$^+$.

g) N-(5-Amino-6-phenyl-3(2H)-pyridazin-4-yl) Diethyl Phosphoramidate

To the product of Example 1f) (~57 mmol) was added phosphorus oxychloride (150 ml) and N,N-dimethylaniline (30 ml). The mixture was then heated at reflux, with stirring, for 3 hours. The resulting solution was cooled to room temperature, and the excess phosphorus oxychloride was removed by evaporation at reduced pressure. The residue was cooled in an ice bath, and quenched by cautious addition of ethanol (250 ml). The resulting solution was transferred to a 2 l Parr flask, and ethanol (100 ml) was added. 10% Palladium on carbon (5 g) was introduced under a nitrogen atmosphere. The mixture was then hydrogenated at 30 psi pressure of hydrogen gas for 24 hours. The catalyst was removed by filtration, fresh 10% palladium on carbon (5 g) was introduced under a nitrogen atmosphere, and the mixture was then hydrogenated at 30 psi pressure of hydrogen gas for 72 hours. The catalyst was removed by filtration, and the filtrate was evaporated at reduced pressure. The residue was neutralised by addition of aqueous ammonia, and extracted with ethyl acetate. The organic extracts were evaporated at reduced pressure, and the residue was triturated with diethyl ether and decanted to wash out most of the N,N-dimethylaniline. The residual solid was crystallised from ethyl acetate and diethyl ether, and dried in vacuo at 40° C., to afford the title compound, 7.5 g (40%), as a pale yellow solid. $^1$H NMR (360 MHz, CDCl$_3$) δ8.75 (1H, s), 7.73 (1H, br m), 7.63 (21, m), 7.49 (3H, m), 5.26 (2H, br s), 4.17 (4H, m), 1.35 (6H, m); nm/e (ES$^+$) 323 [MH]$^+$.

h) 3-Cyclohexyl-8-phenyl-1H-pyrazino[2,3-d] pyridazin-2-one

To the product of Example 1g) (0.400 g, 1.24 mmol) in dichloromethane (4 ml) and tetrahydrofuran (4 ml) was added cyclohexylglyoxylic acid (0.388 g, 2.4 mmol) and 1,3-dicyclohexylcarbodiimide (0.770 g, 3.7 mmol) and the mixture stirred for 18 hours. The reaction was diluted with 10% methanol i dichloromethane and adsorbed onto silica gel. The crude product was purified by flash chromatography (silica gel, eluent ethyl acetate) to give the product as a cream coloured solid (0.223 g; 58%). $^1$H NMR (400 MHz, DMSO-d$_6$) δ12.80 (1H, bs), 9.49 (1H, s), 8.11 (2H, m), 7.98 (1H, s), 7.57 (3H, m), 6.87 (1H, m), 3.21 (1H, m), 2.00 (2H, m), 1.85 (2H, m), 1.60 (3H, m), 1.36 (3H, m); m/e (ES$^+$) 307 [MH]$^+$.

i) 2-Cyclohexyl-3-(2-ethyl-2H-[1,2,4]triazol-3-ylmethoxy)-5-phenylpyrazino[2,3-d]pyridazine To a solution of the product of Example 1h) (0.200 g, 0.65 mmol), triphenylphosphine (0.275 g, 0.98 mmol) and (2-ethyl-2H-[1,2,4]triazol-3-yl)methanol (prepared as described in WO 98/50385) (0.130 g, 0.98 mmol), at 0° C., was added diethylazodicarboxylate (154 μl, 0.98 mmol) dropwise with stirring. The reaction mixture was then stirred at room temperature for 18 hours. The solvent was removed under reduced pressure and the crude product purified by flash chromatography (silica gel, eluent ethyl acetate). The solid obtained was recrystallised from dichloromethane/ethyl acetate/isohexane to yield the title compound as a cream coloured solid (0.129 g; 47%). $^1$H NMR (400 MHz, DMSO-d$_6$) δ9.69 (1H, s), 8.11 (2H, m), 7.98 (1H, s), 7.57 (3H, m), 6.87 (1H, m), 5.74 (1H, s), 4.18 (2H, q, J 7.2 Hz), 3.21 (1H, m), 2.00 (2H, m), 1.85 (2H, m), 1.60 (3H, m), 1.36 (3H, m), 1.30 (3H, t, J 7.3 Hz); m/e (ES$^+$) 416 [MH]$^+$; Anal. found: C, 66.44; H, 6.00; N, 23.44%. C$_{23}$H$_{25}$N$_7$O requires: C, 66.49; H, 6.06; N, 23.60%.

EXAMPLE 2

2-sec-Butyl-3-(2-ethyl-2H-[1,2,4]triazol-3-ylmethoxy)-5-phenylpyrazino[2,3-d]pyridazine a) 3-sec-Butyl-8-phenyl-1H-pyrazino[2,3-d] pyridazin-2-one

By an entirely analogous method to that used for Example 1h), but utilizing sec-butylglyoxylic acid instead of cyclohexylglyoxylic acid, the title product was prepared as an off-white solid. $^1$H NMR (400 MHz, DMSO-d$_6$) δ12.03 (1H, bs), 9.37 (1H, s), 7.72 (2H, m), 7.56 (3H, m), 1.74 (1H, m), 1.22 (2H, m), 1.13 (3H, d), 0.97 (3H, t, J 7.3 Hz); m/e (ES$^+$) 281 [MH]$^+$.

b) 2-sec-Butyl-3-(2-ethyl-2H-[1,2,4]triazol-3-ylmethoxy)-5-phenylpyrazino[2,3-d]pyridazine By reaction of the product of Example 2a) according to the method of Example 1i), the title compound was prepared as a cream coloured solid. $^1$H NMR (400 MHz, DMSO$_6$) δ9.71 (1H, s), 8.15 (2H, m), 7.99 (1H, s), 7.58 (3H, m), 5.73 (1H, m), 4.19 (2H, q, J 7.2 Hz), 3.35 (1H, m), 1.94 (1H, m), 1.64 (1H, m), 1.31 (6H, m), 0.87 (3H, t, J 7.3 Hz); m/e (ES$^+$) 390 [MH]$^+$; Anal. found: C, 64.04; H, 5.91; N, 24.62%. C$_{21}$H$_{23}$N$_7$O.(0.2H$_2$O) requires: C, 64.17; H, 6.00; N, 24.94%.

EXAMPLE 3

2-Cyclopropyl-3-(2-ethyl-2H-[1,2,4]triazol-3-ylmethoxy)-5-phenylpyrazino[23-d]pyridazine a) 3-Cyclopropyl-8-phenyl-1H-pyrazino[2.3-d] pyridazin-2-one

By an entirely analogous method to that used for Example 1h), but utilizing cyclopropylglyoxylic acid instead of cyclohexylglyoxylic acid, the title product was prepared as a yellow solid. $^1$H NMR (400 MHz, DMSO-d$_6$) δ12.43 (1H, bs), 9.37 (1H, s), 7.72 (2H, m), 7.56 (3H, m), 2.61 (1H, m) 1.31 (4H, m); m/e (ES$^+$) 265 [MH]$^+$.

b) 2-Cyclopropyl-3-(2-ethyl-2H-[1,2,4]triazol-3-ylmethoxy)-5-phenylpyrazino[2,3-d]pyridazine By reaction of the product of Example 3a) according to the method of Example 1i), the title compound was prepared as a cream solid. $^1$H NMR (360 MHz, DMSO-d$_6$) δ9.57 (1H, s), 8.15 (2H, m), 8.00 (1H, s), 7.57 (3H, m), 5.74 (1H, s), 4.21 (2H, q, J 7.2 Hz), 2.61 (1H, m), 1.31 (7H, m); m/e (ES$^+$) 374 [MH]$^+$. Anal. found: C, 63.86; H, 4.97; N, 25.88%. C$_{20}$H$_{19}$N$_7$O.(0.1H$_2$O) requires: C, 64.02; H, 5.16; N, 26.13%.

EXAMPLE 4

3-(2-Ethyl-2H-[1,2,4]triazol-3-ylmethoxy)-2-(furan-2-yl)-5-phenylpyrazino[2,3-d]pyridazine a) 3-(Furan-2-yl)-8-phenyl-1H-pyrazino[2.3-d] pyridazin-2-one

By an entirely analogous method to that used for Example 1h, but utilizing (2-furyl)glyoxylic acid instead of cyclohexylglyoxylic acid, the title product was prepared as a yellow solid. $^1$H NMR (400 MHz, DMSO-d$_6$) δ12.9 (1H, bs), 9.45 (1H, s), 8.13 (1H, s), 7.96 (1H, d, J 3.0 Hz), 7.77 (2H, bs), 7.57 (3H, bs), 6.81 (1H, bs); m/e (ES$^+$) 291 [MH]$^+$.

b) 3-(2-Ethyl-2H-[1,2,4]triazol-3-ylmethoxy)-2-(furan-2-yl)-5-phenylpyrazino[2,3-d]pyridazine By reaction of the product of Example 4a according to the method of Example 1i, the title compound was prepared as a pale yellow solid. $^1$H NMR (400 MHz, DMSO-d$_6$) δ9.44 (1H, s), 8.19 (3H, m), 8.04 (1H, s), 7.67 (1H, d, J 3.4 Hz), 7.59 (3H, m), 6.87 (1H, m), 5.85 (1H, s), 4.20 (2H, q, J 7.2 Hz), 1.30 (3H, t, J 7.3 Hz); m/e (ES$^+$) 400 [MH]$^+$; Anal. found: C, 62.68; H, 4.07; N, 24.17%. C$_{21}$H$_{17}$N$_7$O$_2$.(0.1H$_2$O) requires: C, 62.86; H, 4.32; N, 24.43%.

EXAMPLE 5

2-tert-Butyl-3-(2-ethyl-2H-[1,2,4]triazol-3-ylmethoxy)-5-phenylpyrazino[2,3-d]pyridazine a) 3-tert-Butyl-8-phenyl-1H-pyrazino[2,3-d] pridazin-2-one

By an entirely analogous method to that used for Example 1h, but utilizing tert-butylglyoxylic acid instead of cyclohexylglyoxylic acid, the title product was obtained. $^1$H NMR (360 MHz, CDCl$_3$) δ 9.72 (1H, bs), 9.38 (1H, s), 7.68 (2H, m), 7.55 (3H, m), 1.44 (9H, s).

b) 2-tert-Butyl-3-(2-etlhyl-2H-[1,2,4]triazol-3-ylmethoxy)-5-phenylpyrazinol[2,3-d]pyridazine By reaction of the product of Example 5a) according to the method of Example 1i), the title compound was prepared. Recrystallisation from ethyl acetate/diethyl ether afforded colourless needles. $^1$H NMR (400 MHz, DMSO-$d_6$) δ9.69 (1H, s), 8.14 (2H, m), 8.00 (1H, s), 7.58 (3H, m), 5.77 (2H, s), 4.15 (2H, q, J 7.2 Hz), 1.47 (9H, s), 1.29 (3H, t, J 7.2 Hz); m/e (ES$^+$) 390 [MH]$^+$; Anal. found: C, 64.31; H, 5.91; N, 25.09%. $C_{21}H_{23}N_7O.(0.125H_2O)$ requires: C, 64.39; H, 5.98; N, 25.03%.

EXAMPLE 6

2-tert-Butyl-3-(1-methyl-1H-[1,2,4]triazol-3-ylmethoxy)-5-phenylpyrazino[2,3-d]pridazine By reaction of the product of Example 5a) according to the method of Example 1i), but utilizing (1-methyl-1H-[1,2,4]triazol-3-yl)methanol (prepared as described in WO 98/04559), the title compound was prepared. Recrystallisation from dichloromethane/diethyl ether/isohexane afforded pale yellow needles. $^1$H NMR (400 MHz, CDCl$_3$) δ 9.64 (1H, s), 8.26 (2H, m), 8.05 (1H, s), 7.53 (3H, m), 5.64 (2H, s), 3.94 (3H, s), 1.52 (9H, s); m/e (ES$^+$) 376 [MH]$^+$.

EXAMPLE 7

2,5-Diphenyl-3-(2-ethyl-2H-[1,2,4]triazol-3-ylmethoxy)pyrazino[2,3-d]pyridazine a) 3,8-Diphenyl-1H-pyrazino[2,3-d]pyridazin-2-one By an entirely analogous method to that used for Example 1h), but utilizing phenylglyoxylic acid instead of cyclohexylglyoxylic acid, the title product was obtained. $^1$H NMR (360 MHz, DMSO-$d_6$) δ12.70 (1H, bs), 9.46 (1H, s), 8.33 (2H, m), 7.78 (2H, m), 7.57 (6H, m); m/e (ES$^+$) 301 [MH]$^+$.

b) 2,5-Diphenyl-3-(2-ethyl-2H-[1,2,4]triazol-3-ylmethoxy)pyrazino[2,3-d]pyridazine By reaction of the product of Example 7a) according to the method of Example 1i) the title compound was prepared. Recrystallisation from dichloromethane/diethyl ether/isohexane afforded a yellow solid. $^1$H NMR (400 MHz, DMSO-$d_6$) δ9.79 (1H, s), 8.18 (2H, m), 8.13 (2H, m), 7.97 (1H, s), 7.58 (6H, m), 5.78 (2H, s), 4.13 (2H, q, J 7.2 Hz), 1.19 (3H, t, J 7.2 Hz); m/e (ES$^+$) 410 [MH]$^+$; Anal. found: C, 66.53; H, 4.69; N, 23.71%. $C_{23}H_{19}N_7O.(0.25H_2O)$ requires: C, 66.73; H, 4.75; N, 23.68%.

EXAMPLE 8

2,5-Diphenyl-3-(1-methyl-1H-[1,2,4]triazol-3-ylmethoxy)pyrazino[2,3-d]pyridazine By reaction of the product of Example 7a) according to the method of Example 1i), but utilizing (1-methyl-1H-[1,2,4]triazol-3-yl)methanol, the title compound was prepared. Recrystallisation from dichloromethane/diethyl ether/isohexane afforded a yellow solid. $^1$H NMR (400 MHz, DMSO-$d_6$) δ9.77 (1H, s), 8.51 (1H, s), 8.23 (4H, m), 7.58 (6H, m), 5.62 (2H, s), 3.88 (3H, s); m/e (ES$^+$) 396 [MH]$^+$.

EXAMPLE 9

3-(2-Methyl-2H-[1,2,4]triazol-3-ylmethoxy)-5-phenyl-2-(2-thienyl)-pyrazino[2,3-d]pyridazine a) 8-Phenyl-3-(2-thienyl)-1H-pyrazino[2,3-d]pyridazin-2-one By an entirely analogous method to that used for Example 1h), but utilizing (2-thienyl)glyoxylic acid instead of cyclohexylglyoxylic acid, the title product was obtained. $^1$H NMR (360 MHz, DMSO-$d_6$) δ12.80 (1H, vbs), 9.43 (1H, s), 8.52 (1H, m), 8.01 (1H, m), 7.80 (2H, m), 7.58 (5H, m), 7.31 (1H, m); m/e (ES$^+$) 307 [MH]$^+$.

b) 3-(2-Methyl-2H-[1,2,4]triazol-3-ylmethoxy)-5-phenyl-2-(2-thienyl)-pyrazino[2,3-d]pyridazine By reaction of the product of Example 9a) according to the method of Example 1i), but utilizing (2-methyl-2H-[1,2,4]triazol-3-yl)methanol (prepared as described in WO 98/04559), the title compound was prepared. Recrystallisation from dichloromethane/methanol afforded a yellow solid. $^1$H NMR (400 MHz, DMSO-$d_6$) δ9.70 (1H, s), 8.33 (1H, m), 8.15 (2H, m), 8.06 (1H, m), 8.00 (1H, s), 7.60 (3H, m), 7.35 (1H, m), 5.85 (2H, s), 3.86 (3H, s); m/e (ES$^+$) 402 [MH]$^+$; Anal. found: C, 59.29; H, 3.90; N, 23.86%. $C_{20}H_{15}N_7OS.(0.25H_2O)$ requires: C, 59.17; H, 3.85; N, 24.15%.

What is claimed is:
1. A compound of formula I, or a salt thereof:

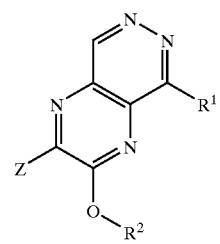

(I)

wherein:
Z represents $C_{1-6}$ alkyl, $C_{3-7}$ cycloalkyl, $C_{4-7}$ cycloalkenyl, $C_{6-8}$ bicycloalkyl, phenyl, naphthyl, azetidinyl, pyrrolidinyl, piperidinyl, piperazinyl, morpholinyl, thiomorpholinyl, diazepanyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, or di($C_{1-6}$) alkylamino, which groups are unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycioalkyl($C_{1-6}$)alkoxy, $C_{3-7}$ cycloalkoxy, amino($C_{1-6}$)alkyl, di($C_{1-6}$)alkylamino ($C_{1-6}$)alkyl, di($C_{1-6}$)alkylamino-carbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$) alkylmorpholinyl($C_{1-6}$)alkyl and imidazolyl ($C_{1-6}$)alkyl;

$R^1$ represents $C_{3-7}$ cycloalkyl, phenyl, furyl, thienyl or pyridinyl, which are unsubstituted or substituted with one or more substituents selected from: $C_{1-6}$alkyl, phenyl($C_{1-6}$)alkyl, naphthyl($C_{1-6}$)alkyl, pyridyl($C_{1-6}$) alkyl, halogen, halo($C_{1-6}$)alkyl, cyano, cyano($C_{1-6}$) alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$) alkyl, di($C_{1-6}$)alkylamino($C_{1-6}$)alkyl, di($C_{1-6}$) alkylamino-carbonyl($C_{1-6}$)alkyl, N-($C_{1-6}$) alkylpiperidinyl, pyrrolidinyl($C_{1-6}$)alkyl, piperazinyl ($C_{1-6}$)alkyl, morpholinyl($C_{1-6}$)alkyl, di($C_{1-6}$) alkylmorpholinyl($C_{1-6}$)alkyl and imidazolyl($C_{1-6}$) alkyl; and R² represents C₃₋₇ cycloalkyl(C₁₋₆)alkyl, phenyl(C₁₋₆) alkyl, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl or quinoxalinylmethyl, which groups are unsubstituted or substituted with one or more substituents selected from: C₁₋₆alkyl, phenyl(C₁₋₆)alkyl, naphthyl (C₁₋₆)alkyl, pyridyl(C₁₋₆)alkyl, halogen, halo(C₁₋₆) alkyl, cyano, cyano(C₁₋₆)alkyl, hydroxy, hydroxymethyl, C₁₋₆alkoxy, C₃₋₇ cycloalkyl(C₁₋₆) alkoxy, C₃₋₇ cycloalkoxy, amino(C₁₋₆)alkyl, di(C₁₋₆) alkylamino(C₁₋₆)alkyl, di(C₁₋₆)alkylaminocarbonyl (C₁₋₆)alkyl, N-(C₁₋₆)alkylpiperidinyl, pyrrolidinyl (C₁₋₆)alkyl, piperazinyl(C₁₋₆)alkyl, morpholinyl(C₁₋₆) alkyl, di(C₁₋₆)alkylmorpholinyl(C₁₋₆)alky and imidazolyl(C₁₋₆)alkyl.

2. The compound of claim 1 represented by formula IIA, and salts thereof:

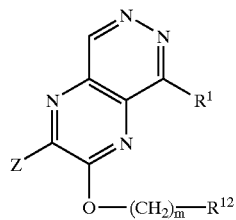

(IIA)

wherein:

m is 1 or 2; and

R¹² represents phenyl, naphthyl, azetidinyl, pyrrolidinyl, piperidinyl, piperazinyl, morpholinyl, thiomorpholinyl, diazepanyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, or tetrazolyl, which groups are unsubstituted or substituted with one or more substituents selected from: C₁₋₆alkyl, phenyl(C₁₋₆)alkyl, naphthyl(C₁₋₆)alkyl, pyridyl(C₁₋₆)alkyl, halogen, halo(C₁₋₆)alkyl, cyano, cyano(C₁₋₆)alkyl, hydroxy, hydroxymethyl, C₁₋₆alkoxy, C₃₋₇ cycloalkyl(C₁₋₆)alkoxy, C₃₋₇ cycloalkoxy, amino(C₁₋₆)alkyl, di(C₁₋₆)alkylamino (C₁₋₆)alkyl, di(C₁₋₆)alkylamino-carbonyl(C₁₋₆)alkyl, N-(C₁₋₆)alkylpiperidinyl, pyrrolidinyl(C₁₋₆)alkyl, piperazinyl(C₁₋₆)alkyl, morpholinyl(C₁₋₆)alkyl, di(C₁₋₆)alkylmorpholinyl(C₁₋₆)alkyl and imidazolyl (C₁₋₆)alkyl.

3. The compound of claim 2 represented by formula IIB, and pharmaceutically acceptable salts thereof:

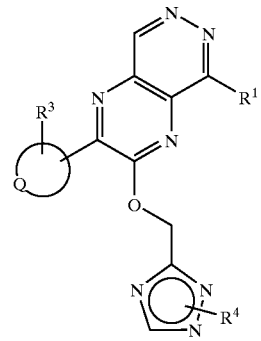

(IIB)

wherein:

Q represents the residue of a cyclopropyl, cyclobutyl, cyclopentyl, cyclohexyl, phenyl, furyl or thienyl ring;

R³ represents hydrogen, methyl or fluoro; and

R⁴ represents methyl or ethyl.

4. The compound of claim 3 wherein Q represents a cyclopropyl, cyclohexyl, phenyl, furyl or thienyl ring.

5. The compound of claim 4 wherein R¹ represents phenyl, fluorophenyl or difluorophenyl.

6. A compound which is selected from the group consisting of:

2-cyclohexyl-3-(2-ethyl-2H-[1,2,4]triazol-3-ylmethoxy)-5-phenyl-pyrazino[2,3-d]pyridazine;

2-sec-butyl-3-(2-ethyl-2H-[1,2,4]triazol-3-ylmethoxy)-5-phenylpyrazino[2,3-]dipyridazine;

2-cyclopropyl-3-(2-ethyl-2H-[1,2,4]triazol-3-ylmethoxy)-5-phenyl-pyrazino[2,3-d]pyridazine;

3-(2-ethyl-2H-[1,2,4]triazol-3-ylmethoxy)-2-(furan-2-yl)-5-phenyl-pyrazino[2,3-d]pyridazine;

2-tert-butyl-3-(2-ethyl-2H-[1,2,4]triazol-3-ylmethoxy)-5-phenyl-pyrazino[2,3-d]pyridazine;

2-tert-butyl-3-(1-methyl-1H-[1,2,4]triazol-3-ylmethoxy)-5-phenyl-pyrazino[2,3-d]pyridazine;

2,5-diphenyl-3-(2-ethyl-2H-[1,2,4]triazol-3-ylmethoxy) pyrazino[2,3-d]pyridazine;

2,5-diphenyl-3-(1-methyl-1H-[1,2,4]triazol-3-ylmethoxy)pyrazino[2,3-d]pyridazine;

3-(2-methyl-2H-[1,2,4]triazol-3-ylmethoxy)-5-phenyl-2-(2-thienyl)-pyrazino[2,3-d]pyridazine;

and salts thereof.

7. A pharmaceutical composition comprising a compound of claim 1 or a pharmaceutically acceptable salt thereof and a pharmaceutically acceptable carrier.

8. A process for the preparation of a compound of claim 1 which comprises reacting a compound of formula III (or its 2-hydroxypyrazino-[2,3-d]pyridazine tautomer) with a compound of formula IV:

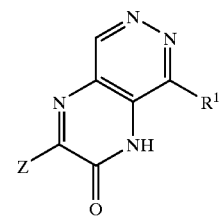

(III)

wherein L¹ represents a suitable leaving group.

9. A method for the treatment of anxiety which comprises administering to a patient in need thereof an effective amount of a compound of claim 1 or a pharmaceutically acceptable salt thereof.

\* \* \* \* \*